(12) United States Patent
Vinding

(10) Patent No.: US 7,104,491 B2
(45) Date of Patent: Sep. 12, 2006

(54) RETRACTABLE REEL FOR FLEXIBLE TUBING

(76) Inventor: Donald R. Vinding, 30794 Calle Chueca, San Juan Capistrano, CA (US) 92675

( * ) Notice: Subject to any disclaimer, the term of this patent is extended or adjusted under 35 U.S.C. 154(b) by 511 days.

(21) Appl. No.: 10/072,011

(22) Filed: Feb. 7, 2002

(65) Prior Publication Data

US 2003/0146332 A1 Aug. 7, 2003

(51) Int. Cl.
*B65H 75/48* (2006.01)

(52) U.S. Cl. .................. 242/378.4; 242/378; 242/385.1
(58) Field of Classification Search ................. 242/378, 242/378.4, 385.1; 137/355.17, 355.23, 355.26
See application file for complete search history.

(56) References Cited

U.S. PATENT DOCUMENTS

| | | | | | |
|---|---|---|---|---|---|
| 3,337,695 | A | * | 8/1967 | Brown | ....................... 191/12.4 |
| 6,371,398 | B1 | * | 4/2002 | Liao | .......................... 242/378.1 |
| 6,375,109 | B1 | * | 4/2002 | Liao | ............................ 242/378 |
| 6,405,961 | B1 | * | 6/2002 | Mastrangelo | ............ 242/378.1 |
| 6,416,005 | B1 | * | 7/2002 | Liao | ........................ 242/378.1 |
| 6,497,378 | B1 | * | 12/2002 | Liao | ........................ 242/378.1 |

* cited by examiner

Primary Examiner—Kathy Matecki
Assistant Examiner—Sang Kim
(74) Attorney, Agent, or Firm—Roy A. Ekstrand

(57) ABSTRACT

A generally cylindrical housing supports a pair of rotatable tubing wheels within the housing. Each rotatable tubing wheel supports a quantity of flexible tubing having one end extending outwardly through an aperture in the housing and the remaining end coupled to a rotatable coupler such that gas flow may be produced between the two outer ends of the two flexible tubings. Each rotatable wheel is operatively coupled to a spring-driven ratchet-controlled winding and rewinding mechanism. The rotatable coupler between the interior ends of the two flexible tubes allows for independent rotation of each tubing wheel with respect to the remaining tubing wheel.

4 Claims, 4 Drawing Sheets

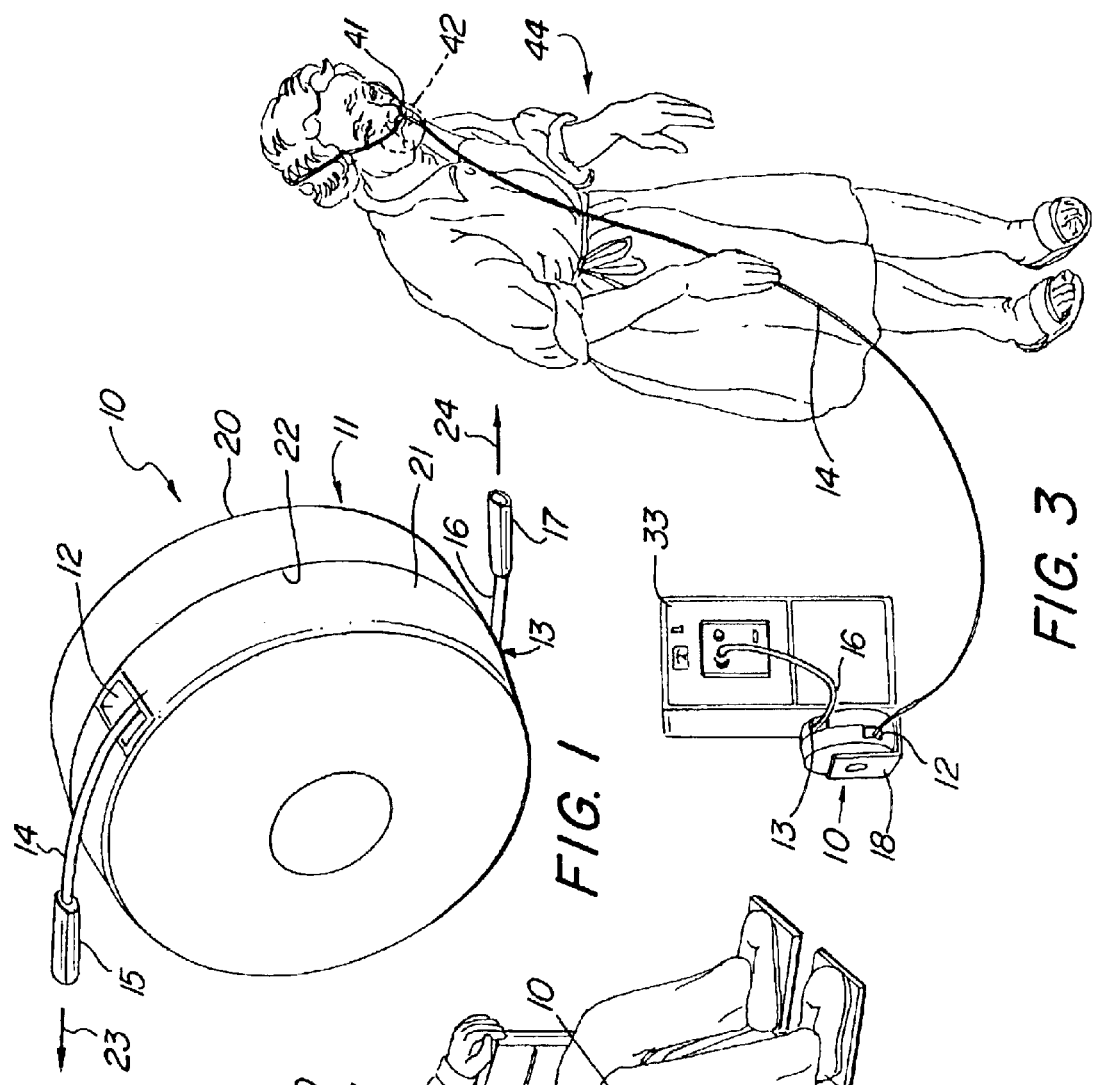
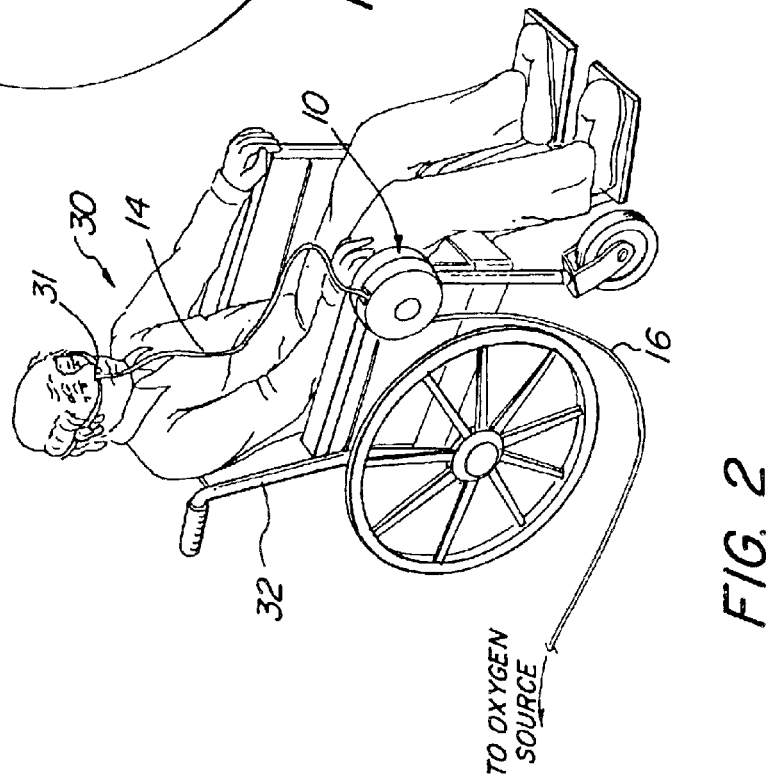
FIG. 1
FIG. 2
FIG. 3

RETRACTABLE REEL FOR FLEXIBLE TUBING

FIELD OF THE INVENTION

This invention relates generally to medical and/or therapeutic uses of respiratory gases such as oxygen or oxygen mixtures and particularly to delivery systems utilized therewith.

BACKGROUND OF THE INVENTION

In the treatment and care of a variety of medical problems, disorders, illnesses as well as aging effects, practitioner's in the medical arts often apply a flow of relatively pure oxygen or an oxygen enriched mixture to the patient for respiration. Often the patient wears a mask or nasal cannula to facilitate breathing the oxygen or oxygen-rich mixture.

In any event, the patient's breathing attachment is typically coupled by a flexible tube or the like to a source of the therapeutic treatment gas. The gas source may be a wall mounted outlet such as that utilized by centralized distribution systems in hospitals and other patient care facilities or a stationary in-room supply. Some degree of mobility is afforded to the patient through the use of small portable compressed gas supplies. However, for the most part, patient's rely upon the more stationary in-room or hospital outlet supplies for their oxygen or other treatment gases.

The use of such stationary gas supplies substantially limits the mobility of the patient in that, the patient is in effect "tethered" to the stationary supply by the flexible tubing.

U.S. Pat. No. 5,392,808 issued to Pierce sets forth a RETRACTABLE TUBING REEL for utilization in conjunction with an oxygen supply tank and a nasal catheter. The device includes a housing supporting a rotatable reel within which a quantity of flexible tubing is wound. A spring within the housing is operatively coupled to the tubing reel to provide a take-up or return force for rewinding withdrawn flexible tubing.

In a closely related art, several patents such as take-up reels for use with electrical cord or the like. For example, U.S. Pat. No. 5,230,481 issued to Weeler et al. sets forth a CORD TAKE-UP DEVICE having a housing defining a pair of adjacent compartments separated by a common interior wall. A cord take-up reel is rotatably supported within each compartment and flat wire cable is received in both sides of the compartment through housing apertures and wound upon its respective reel. A spring provides return or take-up tension to the cord reels.

U.S. Pat. No. 5,422,957 issued to Cummins sets forth a CABLE TAKE-UP FOR EARPHONES having a cylindrical case within which a cable is wound upon a rotating spool. A spring biases the spool toward cable retraction. A ratchet prevents the cable from retracting and a release for the ratchet is accessible from outside the case.

U.S. Pat. No. 5,797,558 issued to Peterson et al. sets forth a UNIDIRECTIONAL CORD TAKE-UP DEVICE for use with flat wire cable. The device includes a generally cylindrical case within which a take-up reel is supported. A spring is supported within the case and coupled to the reel for urging the reel toward cable take-up.

U.S. Pat. No. 5,101,082 issued to Simmons et al. sets forth an ELECTRIC POWER CORD TAKE-UP REEL WITH AUTOMATICALLY OPERATED LATCH PAWL ACTUATED SWITCHING MECHANISM having an external housing, a shaft mounted in the housing, and a spool journalled on the shaft for storing a length of electric power cord. A spring biased rewind mechanism returns a length of cord previously withdrawn from the wheel for storage.

U.S. Pat. No. 4,437,624 issued to Rosenberg sets forth a POSITIONING REEL for suspending a body such as a light-weight tool at any vertical position within the limits of the suspension cord. An adjusting screw regulates a clutch-type tensioning break which permits the supporting force of the positioning reel to be set to equalize the weight of the suspended tool. As a result, little effort is required to raise or lower the suspended tool.

U.S. Pat. No. 4,008,791 issued to Shafii-Kahany et al. sets forth a still further variation of take-up reel apparatus for entitled TAKE-UP REEL FOR COMBINED HOSE AND CABLE. U.S. Pat. No. 5,147,265 issued to Pauls et al. sets forth a ROTATION-ACTIVATED RESISTANCE DEVICE while U.S. Pat. No. 4,917,362 issued to Wilson sets forth an AUTOMATIC WIRE PULLER both having structures generally related to the present invention environment.

U.S. Pat. No. 4,488,014 issued to Daniel et al. sets forth an REELING ASSEMBLY for use in an environment such as fabric drying or the like.

While the foregoing described prior art devices have to some extent improved the art and have in some instances enjoyed commercial success, there remains nonetheless a continuing need in the art for a more improved apparatus for managing an increased length of flexible tubing for patients utilizing oxygen.

SUMMARY OF THE INVENTION

Accordingly, it is a general object of the present invention to provide an improved take-up device for flexible tubing. It is more particular object of the present invention to provide an improved take-up device for flexible tubing fabricated for use within the home as well as within medical and medical treatment facilities.

In accordance with the present invention there is provided a retractable reel for flexible tubing comprising: a housing defining an interior cavity and first and second apertures; a first tubing wheel rotatably supported within the housing; a first spring coupled to the first wheel urging the first wheel toward a first winding direction of rotation; a first ratchet pawl mechanism coupled to the first wheel for releasably latching the wheel against rotation in the first winding direction of rotation; a first flexible tube wound upon the first wheel having a first internal end and a first external end, the first external end and a portion of the first flexible tube passing outwardly through the first aperture; a second tubing wheel rotatably supported within the housing; a second spring coupled to the second wheel urging the second wheel toward a second winding direction of rotation; a second ratchet pawl mechanism coupled to the second wheel for releasably latching the wheel against rotation in the second winding direction of rotation; a second flexible tube wound upon the second wheel having a second internal end and a second external end, the second external end and a portion of the second flexible tube passing outwardly through the second aperture; a rotatable coupler connected between the first and second internal ends, whereby the first and second flexible tubes may be independently wound upon or withdrawn from the first and second tubing wheels respectively.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 1 sets forth a perspective view of a retractable reel for flexible tubing constructed in accordance with the present invention;

FIG. 2 sets forth a perspective view of the present invention retractable reel for flexible tubing in a typical use with a wheelchair patient;

FIG. 3 sets forth a perspective view of a retractable reel for flexible tubing constructed in accordance with the present invention in a typical use with a walking patient;

DESCRIPTION OF THE PREFERRED EMBODIMENT

Figure 4:
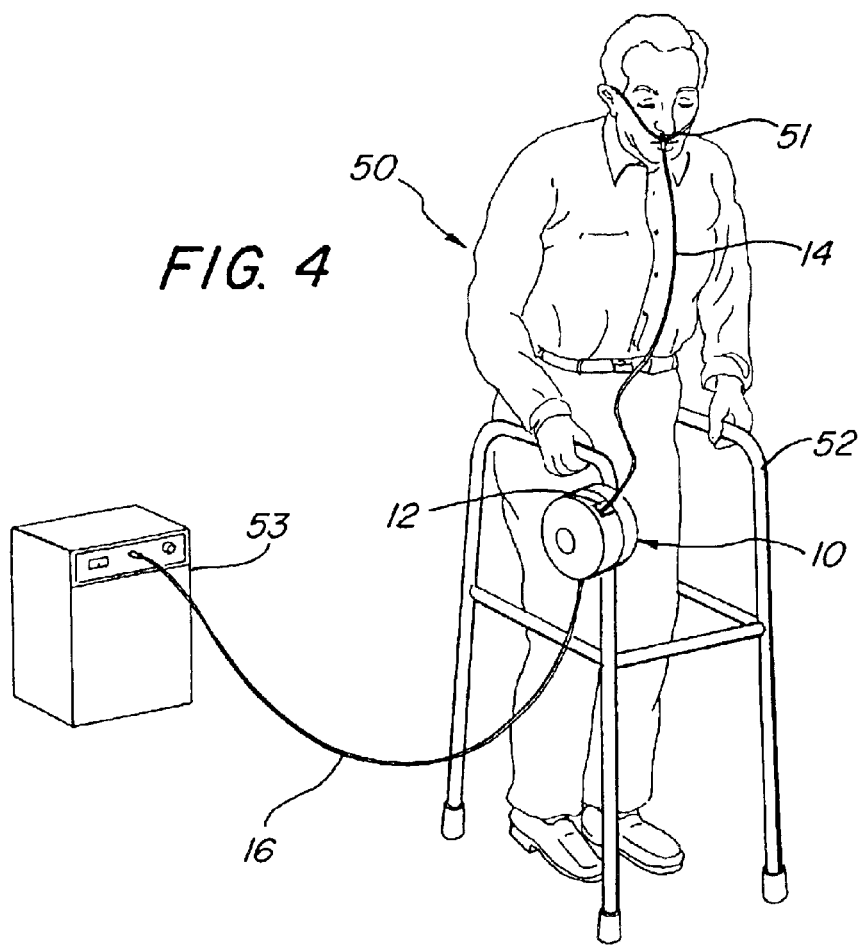
FIG. 4 sets forth a perspective view of a retractable reel for flexible tubing constructed in accordance with the present invention in a typical use by a walker-assisted patient.

FIG. 1 sets forth a perspective view of a retractable reel for flexible tubing constructed in accordance with the present invention and generally referenced by numeral 10. Retractable reel 10 includes a generally cylindrical housing 11 preferably formed of a molded plastic material or the like and having a pair of generally mirror image half portions 20 and 21 joined along common mating surfaces 22 to form a generally enclosed housing. The apparatus within housing 11 which is set forth below in greater detail, supports a pair of flexible tubes 14 and 16. Flexible tubes 14 and 16 are supported within housing 20 by apparatus described below and extend outwardly through apertures 12 and 13 and terminate in fittings 15 and 17 respectively. Aperture 13 is better seen in FIG. 6.

In accordance with the present invention, retractable reel 10 supports a pair of flexible tubes such as oxygen supply tubes which are wound upon respective tubing wheels within housing 11 in a spring-driven and ratchet-controlled apparatus. Accordingly, with retractable reel 10 secured in the various manners set forth below in FIGS. 2 through 5, flexible tubes 14 and 16 may be drawn outwardly in the directions indicated by arrows 23 and 24 to facilitate coupling to a source of therapeutic gas such as oxygen and to administering device such as a conventional cannula. In accordance with an important aspect of the present invention, the oppositely oriented ratchet pawl mechanism controlled tubing wheels supported within housing 11 are operative in the manner below in greater detail to facilitate flexible use of the oxygen administering system with which the present invention cooperates. For example, the independent operation of the storing and winding mechanisms for tubes 14 and 16 within housing 10 facilitate complete freedom of movement for variable distances between retracting reel 10 and the oxygen source as well as retractable reel 10 and the patient user. This dual capability greatly enhances the ease of use and avoids safety problems often created by prior art devices which tend to encourage the user to unreel a substantial length of tubing to facilitate movement while the therapeutic gas is being administered.

FIG. 2 sets forth a perspective view of the present invention retractable reel for flexible tubing generally referenced by numeral 10 in a typical use for a wheelchair patient generally referenced by numeral 30. In accordance with conventional needs, a wheelchair patient 30 is seated within a conventional wheelchair 32. In accordance with the present invention, retractable reel 10 is secured to wheelchair 32 using conventional fastening and bracketing means (not shown). In further accordance with the present invention, retractable reel 10 supports a first flexible tube 14 extending upwardly from aperture 12 of retractable reel 10 to couple to a conventional cannula 31 worn by patient 30. In further accordance with the present invention, a second flexible tube 16 extends downwardly from retractable reel 10 and is coupled to a source of therapeutic gas such as oxygen (not shown).

In accordance with the present invention, the independent adjustment capability of flexible tubes 14 and 16 allows wheelchair patient 30 to conveniently adjust the extension of flexible tube 14 from reel 10 independently from the adjustment of flexible tube 16. As a result, the user may, for example, move wheelchair 32 changing the distance between the user and the oxygen source which is accommodated by flexible tube 16 without affecting the slack or tension opposed upon flexible tube 14. Conversely, wheelchair patient 30 may maintain the position of wheelchair 32 leaving the extension of flexible tube 16 at the desired length while exercising movement away from wheelchair 32 which is facilitated by the independent extension of flexible tube 14 from retractable reel 10. As can be seen, a minimal amount of flexible tubing is left in a slack position while a maximum amount of patient flexibility is afforded by the present invention retractable reel for flexible tubing.

FIG. 3 sets forth a perspective view of the present invention retractable reel for flexible tubing generally referenced by numeral 10 utilized in a typical application with a walking patient generally referenced by numeral 40. Retractable reel 10 is supported within a bracket 18 upon an oxygen source 33. Oxygen source 33 is fabricated in accordance with conventional fabrication techniques and typically provides a storage of one or more pressurized containers of oxygen together with appropriate pressure regulation and dispensing apparatus (not shown) all of which may be entirely conventional in operation. In accordance with the present invention, retractable reel 10 defines apertures 12 and 13 through which flexible tubes 16 and 14 extend from reel 10. In the manner of application of FIG. 3, flexible tube 16 is coupled to oxygen source 33 by conventional connecting means (not shown) while flexible tube 14 is coupled to a cannula 41 worn by patient 40 also in accordance with conventional fabrication. Alternatively, cannula 41 may be replaced by an alternative dispensing mechanism such as a mask 42 shown in dashed-line representation.

In accordance with an important advantage of the present invention, it will be noted that patient 40 is able to freely walk toward or away from oxygen source 33 as retractable reel 10 dispenses or withdraws a suitable length of flexible tube 14. In the event it became necessary to couple flexible tube 16 to an alternative oxygen source, flexible tube 16 would be readily moveable from oxygen source 33 without disturbing the length of flexible tube 14.

FIG. 4 sets forth a perspective view of a retractable reel for flexible tubing constructed in accordance with the present invention and generally referenced by numeral 10. Retractable reel 10 is shown in FIG. 4 in a typical application for a walker-assisted patient generally referenced by numeral 50. Patient 50 utilizes a conventional walker apparatus 52 for aide and support in moving about. In accordance with the preferred application of the present invention, retractable reel 10 is preferably secured to walker 52 using a conventional attachment bracket (not shown). The important aspect of attachment of retractable reel 10 to walker 52 is the use of a secure mechanical connection.

Patient 50 utilizes a conventional cannula 51 coupled to flexible tube 14 of retractable reel 10. Similarly, flexible tube 16 of retractable reel 10 is coupled to a conventional oxygen source 53.

In accordance with an important aspect of the present invention, it will be noted that the combination of walker 52 and retractable reel 10 may be moved about by patient 50 producing extension or withdraws of flexible tube 16 without affecting the extension of flexible tube 14 from retractable reel 10. Conversely, patient 50 is able to place walker 52 at a desired location and thereafter move away from walker 52 as desired in a manner which is accommodated by the independent extension or withdraw of flexible tube 14.

Figure 5:
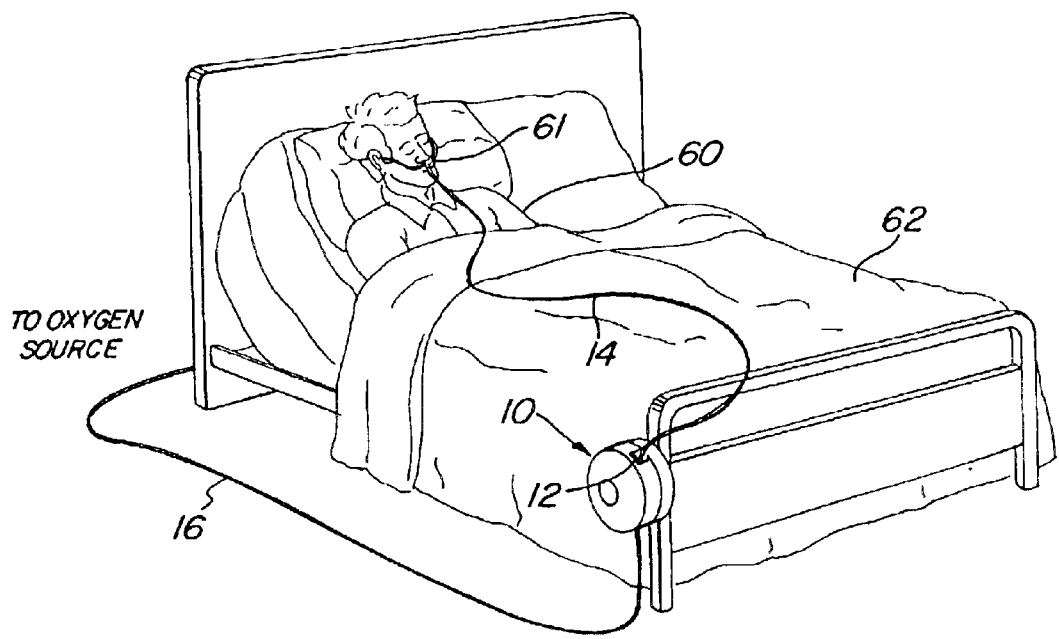
FIG. 5 sets forth a perspective view of a retractable reel for flexible tubing constructed in accordance with the present invention in a typical use by a bed ridden patient.

FIG. 5 sets forth a perspective view of a retractable reel for flexible tubing constructed in accordance with the present invention and generally referenced by numeral 10 which is utilized in combination with a bed-ridden patient generally referenced by numeral 60. Patient 60 is resting within a conventional bed 62 and is wearing a conventional cannula 61. In accordance with the present invention, retractable reel 10 is secured to a convenient portion such as the foot of bed 62 by conventional attachment (not shown). Flexible tube 14 extends outwardly through aperture 12 of retractable reel 10 and is coupled to cannula 61. Flexible tube 16 of retractable reel 10 extends from reel 10 to a source of oxygen or other therapeutic gas (not shown). In accordance with the present invention, the independent extension and withdraw of flexible tubes 14 and 16 with respect to retractable reel 10 allow for independent movement of bed 62 supporting patient 60 without effecting the extension or tension opposed by flexible tube 14. Conversely, the present invention retractable reel allows patient 60 to move within bed 62 or, for that matter, to rise from bed 62 and move about the room in a movement which is accommodated entirely by flexible tube 14 without disturbing the extension or tension within flexible tube 16. In this manner, the present invention retractable reel allows a greater flexibility and safety of use for patient 60.

Figure 6:
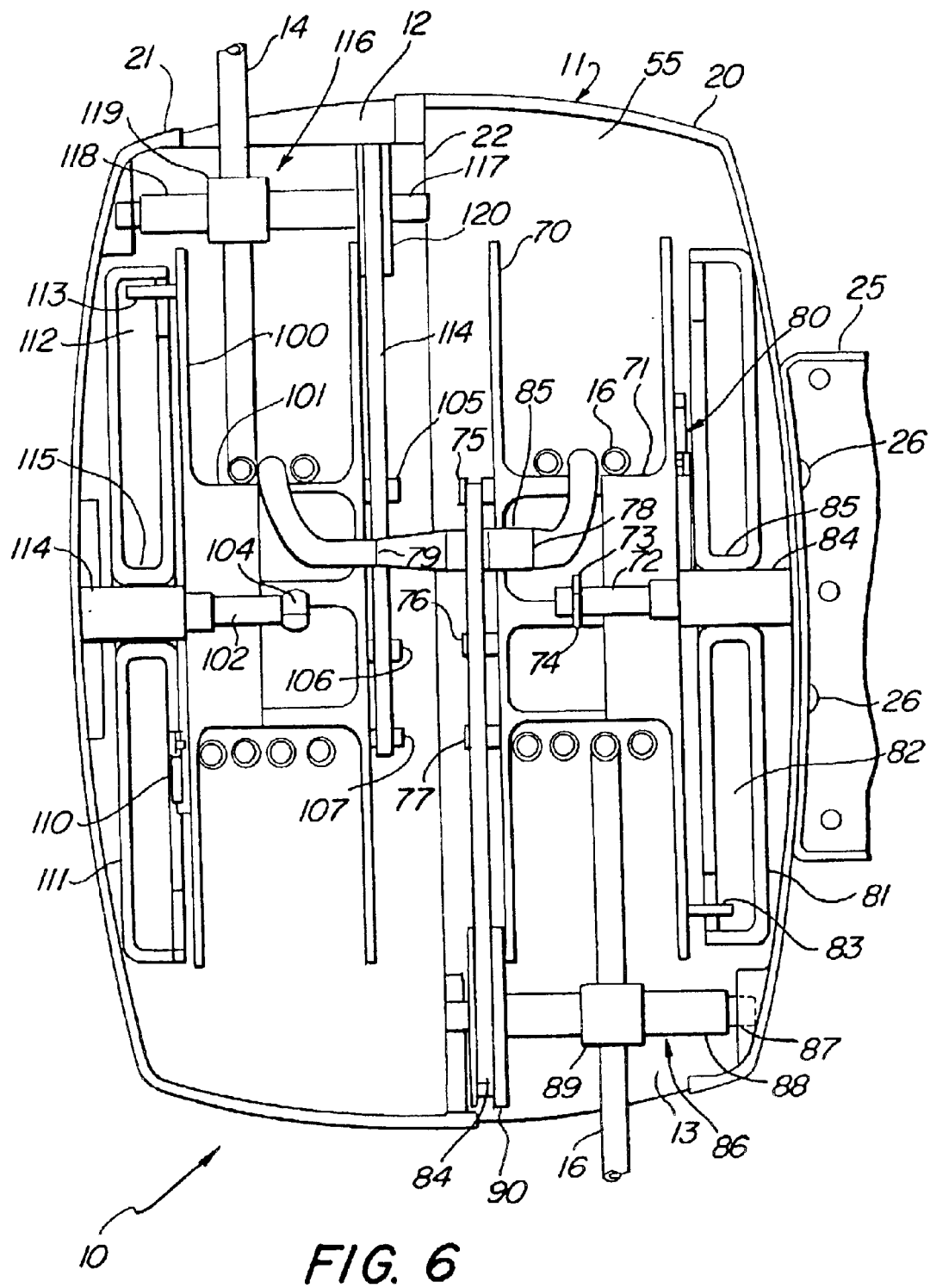
FIG. 6 sets forth a section view of the present invention retractable reel for flexible tubing.

FIG. 6 sets forth a section view of retractable reel 10 showing the positioning and orientation of the operative apparatus therein. For purposes of clarity and ease of understanding, certain conventional structural members and support members within reel 10 have been omitted from FIG. 6 as an aid to understanding and explanation. More specifically, retractable reel 10 includes a housing 11 defining an interior cavity 55 and supporting a conventional attachment bracket 25. By way of overview, housing 11 supports a pair of mirror-image apparatus each utilized in securing and supporting an extendible quantity of flexible tubing. In further overview, the apparatus storing each quantity of flexible tubing are independently moveable and are coupled by a rotatable coupler 85. In this manner, this extension or withdraw of either quantity of flexible tubing from one support apparatus is completely independent of the extension or withdraw of flexible tubing from the remaining apparatus.

More specifically, housing 11 is fabricated of molded plastic half portions 20 and 21 which are joined along a common set of mating surfaces 22. Attachment between half portions 20 and 21 is preferably carried forward by snap-fit attachment. However, other conventional attachments such as adhesive attachment or the like may be utilized without departing from the spirit and scope of the present invention. A rotatable coupler 85 is supported at the approximate center of housing 11 and defines coupling ends 78 and 79 extending in opposite directions. Housing 11 further includes a tubing wheel 70 supporting flexible tube 16 and having a plurality of posts 75, 76 and 77. Housing 11 further defines a boss 84 which supports a shaft 72 having a groove 73 formed therein. Wheel 70 is rotatably supported upon shaft 72 and secured by a clip 74. Boss 84 further supports a rotatable spring housing 81 having a hub 85 upon which a coil spring 82 is secured. By means not shown but in accordance with conventional fabrication techniques, the interior end of coil spring 81 is secured to hub 85. Wheel 70 defines a spring tab 83 which is joined to the outer end of spring 82. A ratchet mechanism 80 (better seen in FIG. 8) is coupled between wheel 70 and spring housing 81. Ratchet mechanism 80 is conventional in operation and structure and is used to control the extension and rewind of flexible tube 16 upon hub 71 of wheel 70.

A level winder mechanism 86 constructed in accordance with conventional fabrication techniques is supported within housing 11 near aperture 13 by a worm shaft 87. Worm shaft 87 further supports a sleeve 88 upon which a feeder 89 is movably supported. A pulley 90 is secured to and rotatable with worm shaft 87. A flexible endless belt 84 is received upon pulley 90 and is wound about posts 75, 76 and 77 in the manner set forth below in FIG. 9.

In further accordance with the present invention, housing 11 supports a second tubing wheel 100 having a hub 101. Housing 11 further includes a cylindrical boss 114 which supports a shaft 102 having a clip 104 on the interior end thereof. Wheel 100 is rotatably supported upon shaft 102 and includes a spring tab 113 and a plurality of posts 105, 106 and 107. A spring housing 111 includes a hub 115 rotatably supported upon boss 114. A coil spring 112 is supported upon hub 115 having an interior end secured thereto (not shown) and an outer end secured to spring tab 113. A conventional ratchet pawl mechanism 110 is coupled between wheel 100 and spring housing 111. A quantity of flexible tubing 14 is wound upon hub 101 and extends outwardly through aperture 12 of housing 11.

Housing 11 further supports a level winder mechanism 116 having a worm shaft 117 rotatably supported within housing 11. A sleeve 118 and a feeder 119 is further supported upon worm shaft 117. The outer end of tube 14 passes through feeder 119 and outwardly through aperture 12. The interior end of tube 14 is joined to end 79 of rotatable coupler 85. An endless belt 114 is received upon pulley 120 and posts 105, 106 and 107.

In operation, the apparatus supporting flexible tube 14 and the apparatus supporting flexible tube 16 operates in an identical fashion in complete independence one from another. Accordingly, a quantity of flexible tube 14 is wound upon hub 101 of wheel 100. In the event additional tubing is required for extension from housing 11, the user pulls upon tube 14 overcoming the force of spring 112 causing rotation of wheel 100 and allowing a quantity of tube 14 to be further withdrawn from wheel 100. Ratchet 110 operates in a conventional fashion to permit the outward withdraw of this quantity of tube 14 so long as the tension is imposed upon tube 14. When the user ceases drawing tube 14 outwardly, ratchet 110 operates in accordance with conventional techniques to latch and secure the rotational position of wheel 100 against the force of spring 112. During the rotation of wheel 100, rotatable coupler 85 allows end 79 and the interior end of tube 14 secured thereto to rotate. In addition, the rotation of wheel 100 rotates pulley 120 operating the conventional leveler winder operation of mechanism 116.

When the user desires to withdraw a quantity of tube 14 into the interior of housing 11, the user draws a tension upon tube 14 releasing latch 110 and thereafter allows the force of spring 112 to wind additional lengths of tube 14 upon hub 101 as spring 112 provides a winding force. When the user has reached the desired extension, the user again pulls upon tube 14 latching the ratchet and pawl mechanism of ratchet 110 and securing wheel 100 at the desired rotational position.

During the winding and unwinding operations of wheel 100, level winder 116 operates in accordance with conventional fabrication techniques to move feeder 119 and thereby tube 14 laterally upon sleeve 118 to uniformly wind or unwind tube 14 with respect to hub 101. As mentioned above, winder leveler mechanism 116 may be entirely conventional in fabrication.

The operation of wheel 70 upon tube 16 is identical to the above described operation of wheel 100 upon tube 14. Of importance to recognize with respect to the present invention, is that as the user draws tube 16 outwardly against the force of spring 82 or releases tube 216 for winding upon hub 71 the operation is entirely independent of the apparatus controlling wheel 100 and tube 14. In this manner, the independent winding and ratcheting mechanisms operable upon each of tubes 14 and 16 provides the increased flexibility of use and safety which form an important aspect of the present invention.

Figure 7:
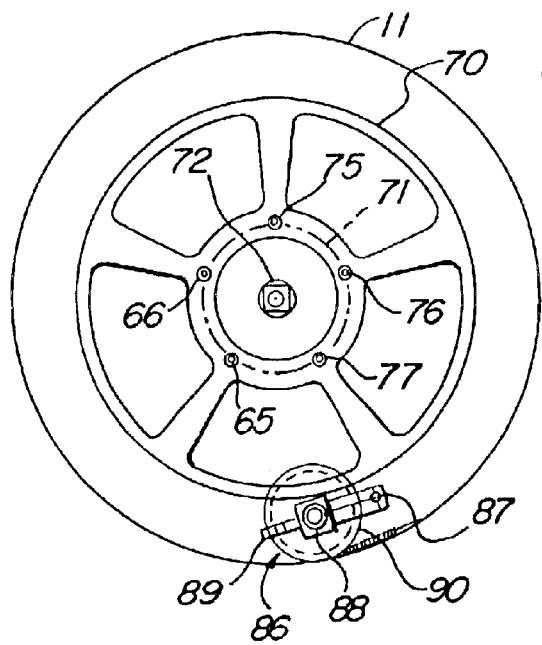
FIG. 7 sets forth a partial side elevation view of a tubing wheel and winding mechanism used in the present invention retractable reel for flexible tubing.

FIG. 7 sets forth a partial side view of wheel 70 and level winder mechanism 86. As described above, wheel 70 includes a hub 71 rotatably supported by a shaft 72. As is also described above, wheel 70 supports a plurality of posts 75, 76 and 77. Additional posts 65 and 66 are further supported on wheel 70 to form a circular arrangement facilitating use of endless belt 84 (seen in FIG. 6).

Level winder mechanism 86 includes a pulley 90 rotatably supported together with a sleeve 88 upon a shaft 87. A feeder 89 is supported upon worm shaft 87 and is moved laterally in accordance with conventional fabrication techniques.

Figure 8:
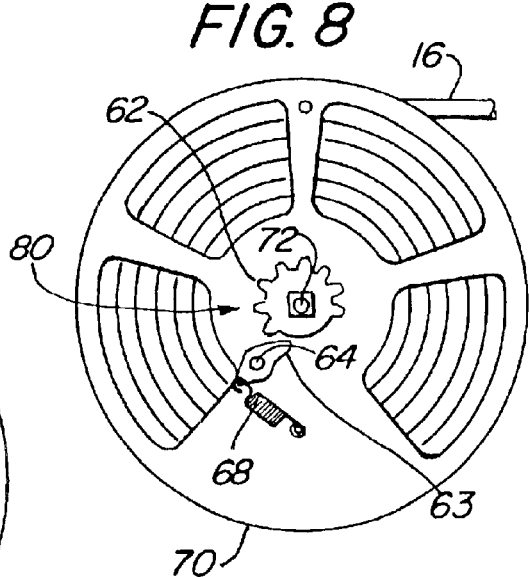
FIG. 8 sets forth a partial side elevation view of the tubing wheel and ratchet mechanism of the present invention retractable wheel for flexible tubing.

FIG. 8 sets forth a partial side view of wheel 70 having a quantity of tube 16 wound thereon. FIG. 8 also shows the apparatus utilized for ratchet mechanism 80. As described above, wheel 70 is rotatably supported upon shaft 72. In accordance with conventional fabrication techniques, ratchet mechanism 80 includes a partial sector gear 62 secured to wheel 70 and moveable therewith upon shaft 72. Mechanism 80 further includes a post 64 supporting a ratchet pawl 63. The outer end of ratchet pawl 63 is secured to a spring 68. The operation of ratchet 80 provides for conventional ratcheted rotation and control of wheel 70. Thus, as tube 16 is drawn outwardly from wheel 70, pawl 63 is moved away from engagement of sector gear 62 due to the resilience of spring 68 and the curvature of pawl 63. When the user releases the tension carefully upon tube 16, sector gear 62 rotates in opposite direction until pawl 63 engages sector gear 62 causing a latch of the rotational position of wheel 70. In further accordance with conventional operation, the user is able to allow tube 16 to be wound upon wheel 70 by releasing tube 16 to facilitate rapid rotation of sector gear 62. The rapid rotation of sector gear 62 prevents pawl 63 from engaging and latching the sector gear and allows tube 16 to be wound upon wheel 70.

Figure 9:
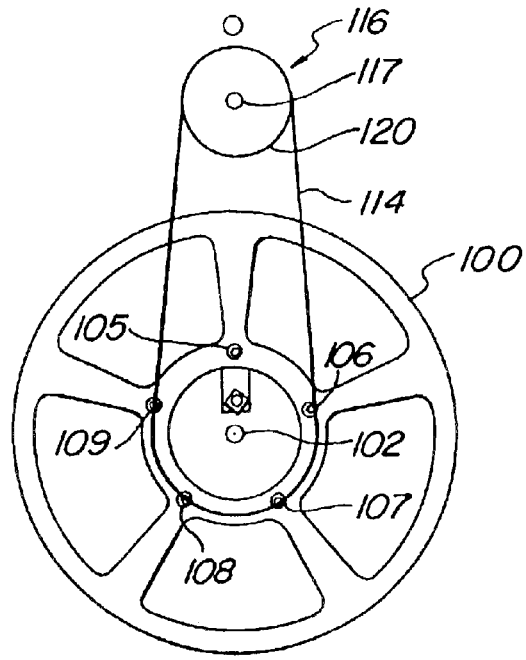
FIG. 9 sets forth a partial side elevation view of a tubing wheel and winding mechanism utilized in the present invention retractable reel for flexible tubing.

FIG. 9 sets forth a partial side elevation view of wheel 100 and level winder mechanism 116. Wheel 100 supports a plurality of posts 105 through 109 which receive one end of an endless flexible belt 114. A shaft 117 supports a pulley 120 which in turn receives the remaining end of endless belt 114. Wheel 100 is rotatable upon a shaft 102 and in accordance with the above described operation is rotated about shaft 102 to dispense or withdraw a quantity of tube 14 (seen in FIG. 6). Of importance with respect to the present invention structure is the coupling of belt 114 between wheel 100 and pulley 120. As a result of this coupling the above described rotation in either direction of wheel 100 upon shaft 102 produces a corresponding rotation of pulley 120 and worm shaft 117. The latter effect produces the leveler winder operation of mechanism 116.

Figure 10:
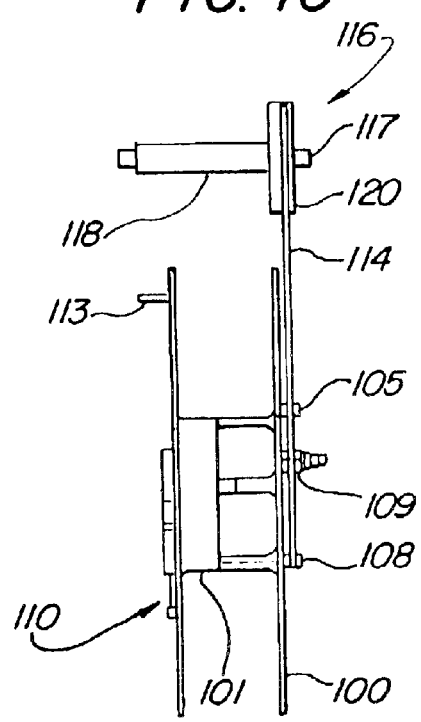
FIG. 10 sets forth a front partial front view of the tubing wheel and winding mechanism shown in FIG. 9 and constructed in accordance with the present invention.

FIG. 10 sets forth a partial front view of wheel 100 and level winder mechanism 116. As described above, wheel 100 includes a hub 101 and a plurality of posts such as posts 105, 108 and 109. A ratchet mechanism 110 is secured to wheel 100 together with a spring tab 113. Level winder mechanism 116 includes a worm shaft 117 and a pulley 120 secured thereto. An endless belt 114 encircles pulley 120 and posts 105 through 109 (seen in FIG. 9) to provide rotational coupling between wheel 100 and pulley 120. A sleeve 118 is received upon worm shaft 117.

What has been shown is a retractable reel for use with flexible tubing such as that used in a therapeutic gas system which provides independent winding and rewinding of a pair of flexible tubes within a common housing. The outer ends of each flexible tube may be readily coupled to a source of therapeutic gas such as oxygen or the like and to a dispensing device such as a conventional cannula for administering the therapeutic gas to a patient. The use of independent internally coupled winding mechanisms for each of the flexible tubes allows independent distancing of the therapeutic gas source and the patient from the retractable reel.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. A retractable reel for flexible tubing comprising:
   a housing defining an interior cavity and first and second apertures;
   a first tubing wheel rotatably supported within said housing;
   a first spring coupled to said first wheel imparting a rotational force upon said first wheel toward a first winding direction of rotation;
   a first ratchet pawl mechanism coupled to said first wheel for releasably latching said wheel against rotation in said first winding direction of rotation;

a first flexible hollow collapsible tube wound upon said first wheel having a first internal end and a first external end, said first external end and a portion of said first flexible tube passing outwardly through said first aperture;

a second tubing wheel rotatably supported within said housing;

a second spring coupled to said second wheel imparting a rotational force upon said second wheel toward a second winding direction of rotation;

a second ratchet pawl mechanism coupled to said second wheel for releasably latching said wheel against rotation in said second winding direction of rotation;

a second flexible hollow collapsible tube wound upon said second wheel having a second internal end and a second external end, said second external end and a portion of said second flexible tube passing outwardly through said second aperture; and a rotatable coupler connected between said first and second internal ends said rotatable coupler being constructed to provide independent rotational coupling between said first and second internal ends, whereby said first and second flexible tubes are independently wound upon or withdraw from said first and second tubing wheels respectively without imparting any twist to said first and second tubes.

2. The retractable reel for flexible tubing set forth in claim 1 wherein said first and second external ends include respective first and second connectors.

3. The retractable reel for flexible tubing set forth in claim 2 wherein said housing is generally cylindrical in shape and wherein said first and second apertures are positioned in generally opposed locations on said housing.

4. The retractable reel for flexible tubing set forth in claim 3 wherein said first and second winding directions are oppositely oriented.

* * * * *